United States Patent [19]
Drucker et al.

[11] Patent Number: 5,571,198
[45] Date of Patent: Nov. 5, 1996

[54] ACETABULAR SHELL WITH SELECTIVELY AVAILABLE BONE SCREW HOLDS

[75] Inventors: David A. Drucker, 210 W. Shearwater Pl. Apt. 51, Jersey City, N.J. 07305; Robert G. Collins, Saddle Brook; Nicholas N. G. Dong, Little Falls, both of N.J.

[73] Assignee: David A. Drucker, New York, N.Y.

[21] Appl. No.: 185,062

[22] Filed: Jan. 21, 1994

[51] Int. Cl.⁶ ............................................ A61F 2/32
[52] U.S. Cl. .................................................. 623/22
[58] Field of Search ............................ 623/16, 18, 21, 623/22, 23

[56] References Cited

U.S. PATENT DOCUMENTS

| | | | |
|---|---|---|---|
| 3,840,904 | 10/1974 | Tronzo . | |
| 3,906,550 | 9/1975 | Rostoker et al. . | |
| 4,285,071 | 8/1981 | Nelson et al. . | |
| 4,417,571 | 11/1983 | Nelson et al. . | |
| 4,563,778 | 1/1986 | Roche et al. . | |
| 4,566,138 | 1/1986 | Lewis et al | 623/22 |
| 4,666,450 | 5/1987 | Kenna . | |
| 4,711,234 | 12/1987 | Vives et al. . | |
| 4,955,325 | 9/1990 | Zarnowski et al. | 623/22 |
| 5,021,062 | 6/1991 | Adrey et al. | 623/22 |
| 5,032,134 | 7/1991 | Lindwer . | |
| 5,041,141 | 8/1991 | Ypma et al. . | |
| 5,282,864 | 2/1994 | Noiles et al. | 623/22 |
| 5,310,408 | 5/1994 | Schryver et al. . | |
| 5,314,487 | 5/1994 | Schryver et al. | 623/22 |
| 5,360,452 | 11/1994 | Engelhardt | 623/22 |
| 5,370,702 | 12/1994 | Jones | 623/22 |

FOREIGN PATENT DOCUMENTS

| | | | |
|---|---|---|---|
| 0346270 | 12/1989 | European Pat. Off. | 623/22 |
| 2638963 | 5/1990 | France | 623/22 |
| 2685192 | 6/1993 | France | 623/22 |

*Primary Examiner*—David Isabella
*Attorney, Agent, or Firm*—Arthur Jacob

[57] ABSTRACT

An improvement in an acetabular cup component of a prosthetic hip implant in which an acetabular shell receives a bearing member within the interior of the acetabular shell and has at least one bone screw hole, the improvement enabling the interoperative selection of implanting the acetabular shell without the employment of a bone screw or with the employment of at least one bone screw for assisting securement of the acetabular shell within the natural bone at the implant site, the improvement including a plug for seating in the bone screw hole to close the bone screw hole, the plug including a fastener arrangement for engaging the acetabular shell to fasten the plug within the bone screw hole, and a sealing arrangement for engaging the acetabular shell essentially to seal the bone screw hole against the migration of debris from the bearing member through the bone screw hole, the fastener arrangement including an operator arrangement for being selectively operated from the interior of the acetabular shell to selectively release the plug from the bone screw hole for removal of the plug through the interior of the acetabular shell to thereby selectively open the bone screw hole for reception of the bone screw.

15 Claims, 2 Drawing Sheets

ACETABULAR SHELL WITH SELECTIVELY AVAILABLE BONE SCREW HOLDS

The present invention relates generally to prosthetic implants and pertains, more specifically, to acetabular cup components employed in connection with prosthetic hip implants.

Improvements in the techniques for replacing a natural hip joint with a prosthetic implant have enabled the procedure to become widely practiced. Among the choices offered to a surgeon in carrying out such a procedure is the manner in which the acetabular cup component of the hip implant will be secured in place in the natural bone. In general, the acetabular cup component includes an acetabular shell constructed of a biocompatible metal and a bearing member constructed of a synthetic polymeric material and placed within the acetabular shell. Depending upon the conditions encountered at the implant site in a particular recipient of the implant, the acetabular cup component can be secured in place either with or without the use of bone screws which extend through the acetabular shell of the acetabular cup component and into the natural bone at the site of the implant.

It has been found that over the service life of an implanted hip prosthesis, the material of the bearing member tends to wear and produce bits of debris. Since it is undesirable for such debris to migrate to the natural tissue surrounding the implant, the integrity of the envelope provided by the acetabular shell must be maintained so as to reduce to a minimum such migration. Where bone screws are employed, the acetabular shell is provided with bone screw holes which interrupt the integrity of the envelope provided by the acetabular shell. However, the bone screw holes receive bone screws and are closed off by the bone screws so as to restore the integrity of the acetabular shell and impede migration of any debris emanating from the material of the bearing member through the acetabular shell to the surrounding natural tissue. Should the implant site permit securement of the acetabular shell without bone screws, as by a simple interference fit or by the use of a suitable cemented securement, the envelope provided by the acetabular shell is unbroken by screw holes and migration of any debris emanating from the material of the bearing member through the acetabular shell to the surrounding natural tissue is precluded.

Thus, acetabular shells are made available in either a configuration which includes bone screw holes or a configuration without bone screw holes, and the surgeon will choose which of the configurations is appropriate for a particular implant procedure. While that choice is dictated by the conditions at the implant site, very often the surgeon is faced with making the decision during the actual implant procedure, when the surgeon can evaluate the conditions at the implant site directly, requiring that the surgeon have the ability to select interoperatively the configuration of choice. Accordingly, acetabular shells of both configurations are made available for selection during the implant procedure, thereby multiplying the expense in carrying out the procedure.

Furthermore, since the use of an acetabular shell of the type having an uninterrupted envelope is preferred, a surgeon may opt for that configuration whenever it appears that the implant site is amenable to that choice; however, upon further evaluation during the actual implant procedure, and even after placement of the selected acetabular shell into the natural bone at the implant site, the surgeon may determine that supplemental securement is necessary after all, requiring removal of the first selected acetabular shell and replacement with an acetabular shell of the type having bone screw holes, thereby prolonging the entire implant procedure.

The present invention avoids the above-described problems by providing an acetabular shell having the desired uninterrupted envelope for the preferred implant without bone screws, and enabling the surgeon to convert the acetabular shell, interoperatively, to a configuration which accepts one or more bone screws, as may be required under the conditions encountered at an implant site during the implant procedure. As such, the present invention attains several objects and advantages, some of which are summarized as follows: Provides the surgeon with the ability to choose a particular acetabular shell securement interoperatively, in response to a direct evaluation of the conditions at the implant site, during the implant procedure, without the necessity of interchanging complete acetabular shells; reduces the time required for the implant of an acetabular shell, as well as the expense involved in the implant procedure; enables increased effectiveness in the securement of an acetabular shell in a hip prosthesis without undue prolongation of the implant procedure; reduces the cost of providing an appropriate acetabular shell configuration for a particular implant site; provides the surgeon with added convenience and increased options for securement of an acetabular shell, during the actual implant procedure, so as to better enable accommodation to the conditions encountered at a particular implant site; effectively minimizes the migration of debris ordinarily emanating from the bearing member of the acetabular cup component to the surrounding natural tissue, during the service life of the hip prosthesis; enables exemplary performance in an acetabular cup component over an extended service life.

The above objects and advantages, as well as further objects and advantages, are attained by the present invention which may be described briefly as an improvement in an acetabular cup component of a prosthetic hip implant, the acetabular cup component being of the type having an acetabular shell which receives a bearing member within the acetabular shell, the acetabular shell having an inner surface defining an interior of the acetabular shell for receiving the bearing member, an outer surface for engagement with the natural bone at an implant site, and at least one bone screw hole in the acetabular shell, the bone screw hole extending through the acetabular shell from the inner surface to the outer surface of the acetabular shell, the improvement enabling the interoperative selection of implanting the acetabular shell without the employment of a bone screw or with the employment of at least one bone screw for assisting securement of the acetabular shell within the natural bone at the implant site, the improvement comprising: a plug for seating in the bone screw hole to close the bone screw hole, the plug including fastener means for engaging the acetabular shell to fasten the plug within the bone screw hole, and sealing means for engaging the acetabular shell essentially to seal the bone screw hole against the migration of debris from the bearing member through the bone screw hole in the direction from the inner surface to the outer surface; the fastener means including operator means for being selectively operated from the interior of the acetabular shell to selectively release the plug from the bone screw hole for removal of the plug through the interior of the acetabular shell to thereby selectively open the bone screw hole for reception of the bone screw.

The invention will be understood more fully, while still further objects and advantages will become apparent, in the following detailed description of preferred embodiments of the invention illustrated in the accompanying drawing, in which.

Figure 1:
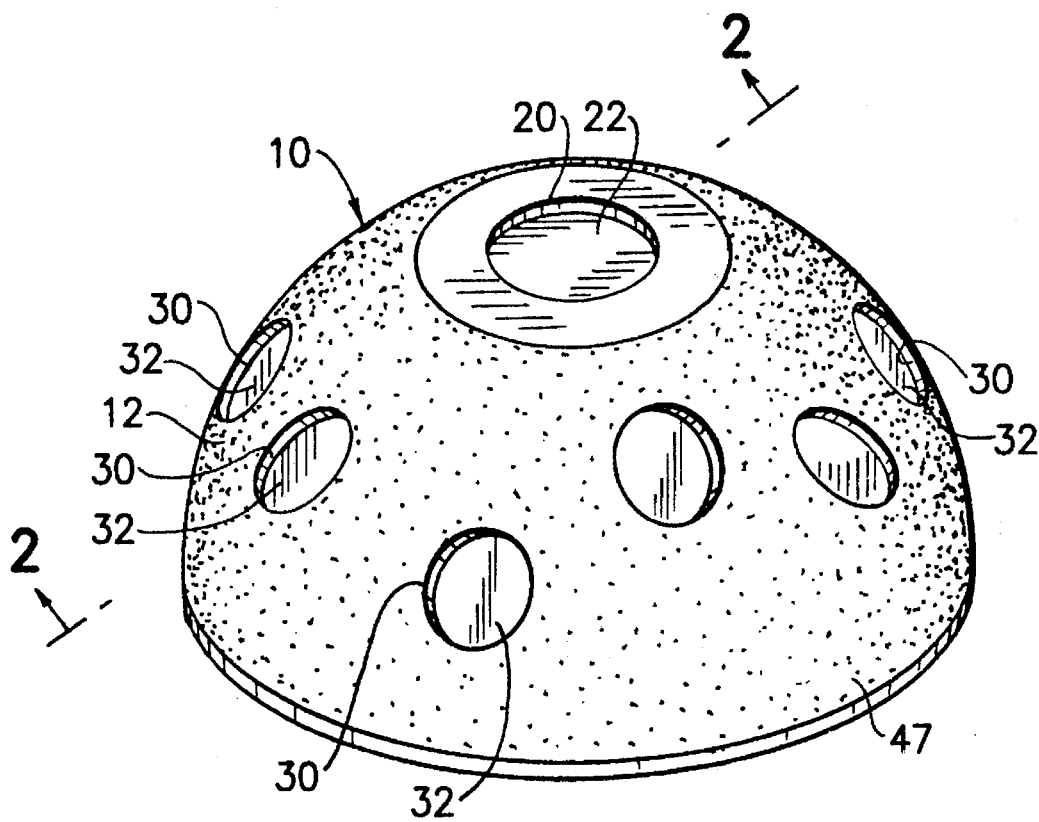
FIG. 1 is a pictorial perspective view of an acetabular shell embodying the improvement of the present invention.
Figure 2:
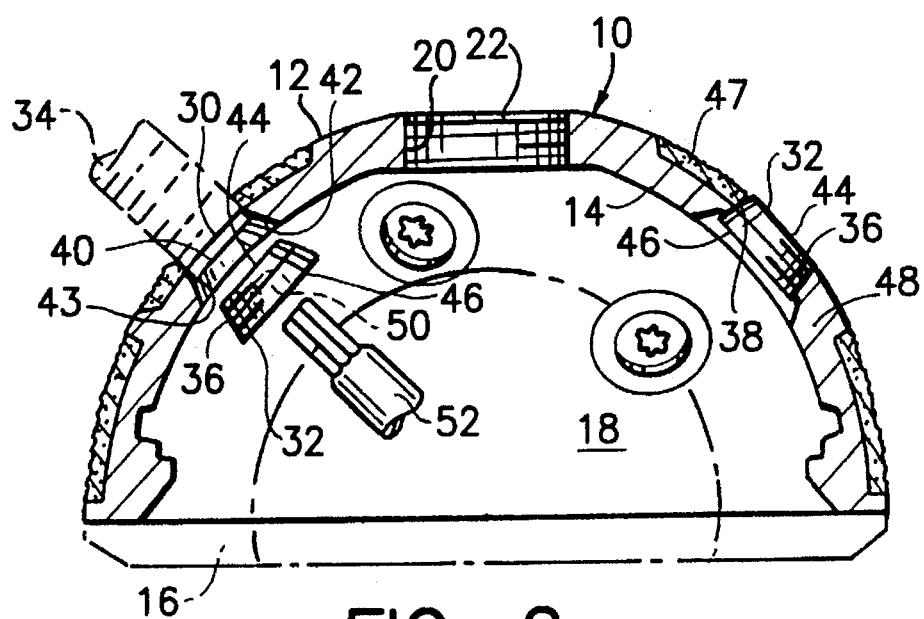
FIG. 2 is an enlarged, partially exploded cross-sectional view taken along line 2—2 of FIG. 1.

Referring now to the drawing, and especially to FIGS. 1 and 2 thereof, an acetabular shell 10 is constructed in a conventional domed configuration and is seen to have an outer surface 12 and an inner surface 14. As is now well-known, the acetabular shell 10 is implanted into the natural bone at an implant site for a prosthetic hip joint and a bearing member, shown in phantom at 16 in FIG. 2, is seated within the interior 18 of the acetabular shell 10 to provide for the reception of a corresponding femoral head (not shown) of the prosthetic hip joint. A threaded opening 20 at the top of the domed configuration of the acetabular shell 10 is engaged with a complementary threaded instrument (not shown) to manipulate and place the acetabular shell 10 in appropriate position at the implant site. Once the acetabular shell 10 is placed in that appropriate position, the instrument is removed and the threaded opening 20 is closed by means of a dome plug 22.

As outlined above, acetabular shells generally are secured in place at an implant site with a suitable cement, or by an interference fit, in which the acetabular shell merely is pressed into place in the natural bone and is secured by carefully chosen differences between the dimensions of the prepared natural bone and the corresponding dimensions of the acetabular shell, or by bone screws which are passed through corresponding bone screw holes in the acetabular shell to be anchored in the natural bone at the implant site. Most often, the choice of one or another of these methods of affixation is dictated by the conditions which exist at the implant site, and these conditions will vary from recipient to recipient. The surgeon must evaluate these conditions and choose the appropriate method of affixation. Since such an evaluation cannot be completed with accuracy prior to commencement of the implant procedure, the surgeon must make the evaluation during the course of the procedure. Accordingly, it becomes necessary for the surgeon to have available immediately an acetabular shell suited to any of the above methods of affixation so as to enable the choice to be accomplished interoperatively.

It is essential that an acetabular shell provide an uninterrupted envelope so that any debris which may emanate from the bearing member during the service life of the implant will not migrate through the acetabular shell to the surrounding natural tissue. Thus, acetabular shells intended for securement with bone screws have been constructed with screw holes which are closed subsequently by the bone screws which secure the acetabular shell in place. Acetabular shells intended to be secured with a suitable cement or by an interference fit have been constructed in the form of a shell, or an envelope, uninterrupted by screw holes. Usually, a surgeon will have available during the implant procedure more than one acetabular shell so that the choice of an appropriate acetabular shell can be made upon direct evaluation of the conditions at the implant site during the course of the implant procedure, thus requiring that a relatively expensive inventory of acetabular shells be maintained for use in connection with only a single procedure.

Acetabular shell 10 eliminates the need for providing separate acetabular shells for the different securement procedures outlined above. Thus, acetabular shell 10 includes a plurality of bone screw holes 30 arrayed throughout the acetabular shell 10, each of which screw holes 30 is closed with a screw hole plug 32 for effectively sealing the screw holes 30 to maintain the required integrity of the envelope provided by the acetabular shell 10. The surgeon is supplied with acetabular shell 10 having all of the screw holes 30 closed with corresponding screw hole plugs 32. Should the surgeon determine, during the course of the implant procedure, that the conditions at the implant site will enable securement of the acetabular shell 10 by means of cement or by an interference fit, the screw hole plugs 32 remain in place to maintain an uninterrupted envelope within which the bearing member 16 will be placed. Should the surgeon determine that bone screws are necessary, one or more of the screw hole plugs 32 merely are removed from the corresponding screw holes 30 and bone screws, one of which is illustrated in phantom at 34 in FIG. 2, are inserted to secure the acetabular shell 10 in place, while at the same time closing off the corresponding screw holes 30.

Figure 4:
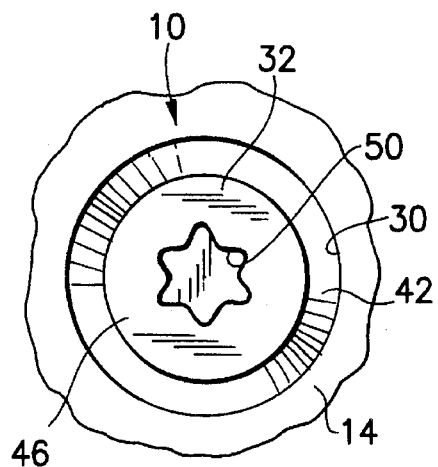
FIG. 4 is a fragmentary plan view taken in the direction of the arrow in FIG. 3.
Figure 3:
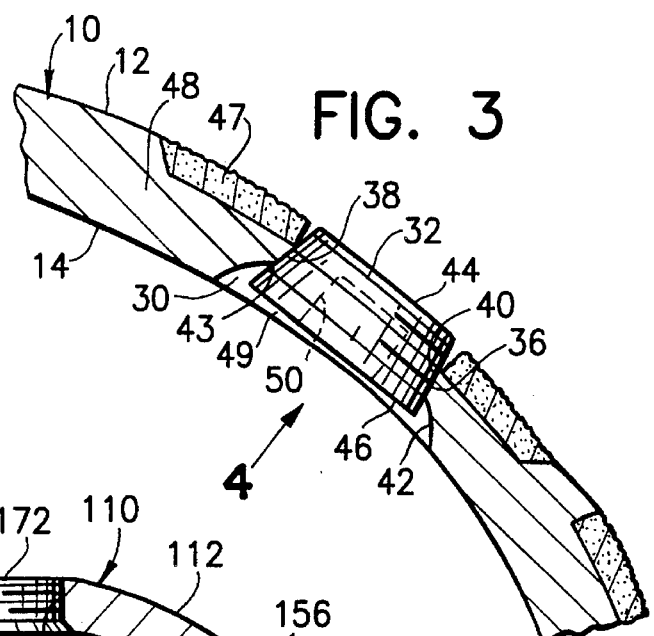
FIG. 3 is a further enlarged fragmentary view of a portion of FIG. 2.

As best seen in FIGS. 3 and 4, each screw hole plug 32 is held in place in a corresponding screw hole 30 by fastener means which engage the screw hole plug 32 with the screw hole 30 to secure the screw hole plug 32 in the screw hole 30. The fastener means include a screw thread 36 on the screw hole plug 32 and a counterpart screw thread 38 in the screw hole 30, the counterpart screw thread 38 being complementary to the screw thread 36 on the screw hole plug 32. In the embodiment of FIGS. 2 and 3, the screw hole 30 includes a bore 40 and a countersink 42. The bore 40 extends from the outer surface 12 toward the inner surface 14 and intersects the countersink 42, which extends from the inner surface 14 toward the outer surface 12, at a shoulder 43. Screw thread 36 is a very fine thread so as to engage the relatively short bore 40 with a purchase sufficient to maintain screw hole plug 32 in place. In the preferred embodiment, screw thread 36 is a microthread, having about one-hundred-twenty-seven threads per inch.

Acetabular shell 10 preferably is constructed of a biocompatible metal, such as titanium, now in common use! for such components. Screw hole plug 32 preferably is constructed of a material having a hardness greater than the hardness of the material of acetabular shell 10 so that upon inserting a screw hole plug 32 into a corresponding screw hole 30, the screw thread 36 will deform the material of the acetabular shell 10, along the bore 40, to establish the counterpart complementary screw thread 38 in the bore 40. A preferred material for screw hole plug 32 is a titanium alloy having a hardness greater than the titanium of the acetabular shell 10.

Screw hole plug 32 is tapered along the axial length of the screw hole plug 32, from a smaller diameter at end 44 toward a larger diameter at opposite end 46. Upon insertion into a screw hole 30, the tapered configuration not only assures appropriate seating of the screw hole plug 32 within the bore 40 of the screw hole 30, but establishes sealing means essentially to seal the screw hole 30 against the migration of debris from the interior 18 of the acetabular shell 10 to the surrounding natural tissue, as described above. The seal established by the sealing means may be characterized as a generally fluid-tight seal effective in minimizing the passage through the plugged screw hole 30 of debris of all particle sizes encountered during the service life of the prosthetic implant.

The axial length of the screw hole plug 32, as compared to the thickness of the acetabular shell 10, between the outer surface 12 and the inner surface 14, is such that upon seating of the screw hole plug 32 in the screw hole 30, the screw hole plug 32 does not protrude beyond the outer surface 12 of the acetabular shell 10. In the illustrated embodiment, the thickness of the acetabular shell 10 includes a sintered coating 47 along at least portions of a shell wall substrate 48 of the acetabular shell 10, which coating 47 enables the screw hole plug 32 to project outwardly beyond the shell wall substrate 48 without extending beyond the outer surface 12; however, the present improvement is not limited to use only with such coated structures. Nor does the screw hole plug 32 protrude inwardly beyond the inner surface 14. Thus, end 46 of screw hole plug 32 is recessed slightly from the inner surface 14 so as to create some clearance, as at 49, between the screw hole plug 32 and the bearing member 16 and assure proper seating of the bearing member 16 within the acetabular shell 10.

Operator means in the form of a drive socket 50 is placed in the screw hole plug 32 at the end 46 so that the screw hole plug 32 is selectively operated from the interior 18 of the acetabular shell 10. While any one of a variety of driving tools may be employed to operate the screw hole plug 32, the preferred configuration for drive socket 50 is the illustrated lobed configuration available commercially under the trademark TORX. Each of the screw hole plugs 32 is selectively removable to expose a screw hole 30 for use, as desired, merely by engaging a driving tool 52 with the drive socket 50 and turning the driving tool 52 to release and remove the screw hole plug 32. Thus, a surgeon may determine at any time during the implant procedure that a bone screw is needed at a particular location and may release and remove the appropriate screw hole plug 32 to expose the corresponding screw hole 30 for use in connection with a bone screw. Since the screw hole plugs 32 are accessible through the interior 18 of the acetabular shell 10, a screw hole 30 may be exposed for use even after the acetabular shell 10 is secured at the implant site. Thus, should the surgeon decide, after securing the acetabular shell 10 by means of cement or an interference fit, that a supplemental bone screw is necessary, the surgeon need merely remove an appropriate screw hole plug 32 and insert the supplemental bone screw. In this manner, the need for removal and replacement of the acetabular shell 10 itself is eliminated, with the concomitant reduction in time, trauma and expense.

Figure 5:
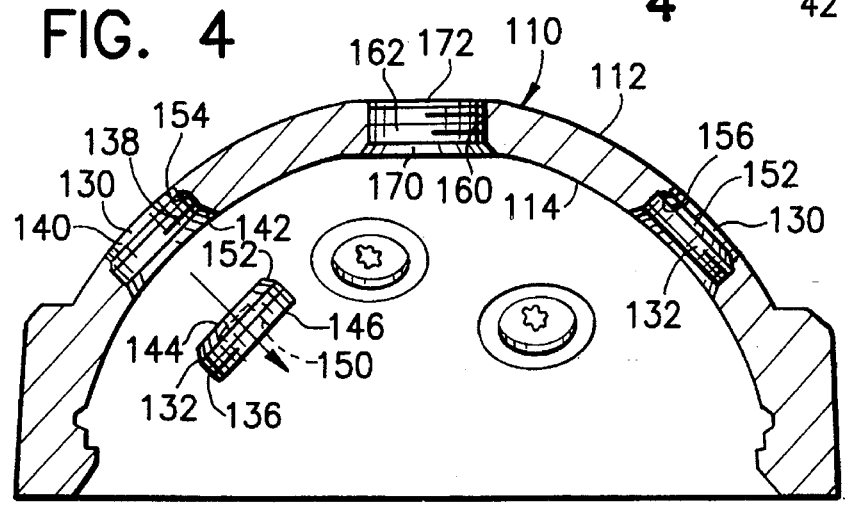
FIG. 5 is a cross-sectional view similar to FIG. 2, but showing another embodiment of the invention.
Figure 6:
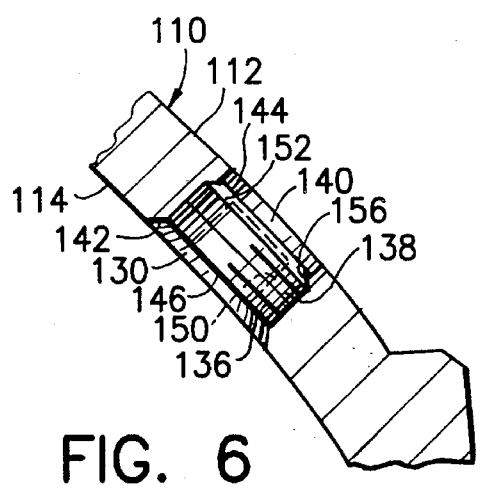
FIG. 6 is an enlarged fragmentary view of a portion of FIG. 5.

In the embodiment of FIGS. 5 and 6, acetabular shell 110 is of the type having a relatively thinner wall thickness between the outer and inner surfaces 112 and 114, respectively, as compared to the total thickness provided by the added coating of the embodiment of FIGS. 1 through 4. Screw holes 130 are closed by screw hole plugs 132 which do not protrude beyond the outer surface 112 of the acetabular shell 110. Here again, the screw hole plugs 132 each carry a screw thread 136 for engagement with a counterpart screw thread 138 within the screw holes 130. The screw holes 130 each include a bore 140 and a countersink 142; however, in order to gain a sufficient purchase for securing the screw hole plug 132 within the screw hole 130, by means of the screw threads 136 and 138, screw thread 138 is located in the countersink 142 so as to provide a secure threaded arrangement once the screw hole plug 132 is seated within the screw hole 130. Screw hole plug 132 extends between opposite ends 144 and 146, and screw thread 136 is located adjacent end 146. As in the earlier-described embodiment, a drive socket 150 is placed in the screw hole plug 130 at the end 146.

Sealing means is provided in the form of a tapered portion 152 of screw hole plug 132, which tapered portion 152 engages the screw hole 130 at the intersection 154 between the bore 140 and the countersink 142 to deform the material of the acetabular shell 110 into a sealing portion in the form of a complementary tapered seat 156 for sealing the screw hole 130 essentially against the migration of debris through the acetabular shell 110 to the surrounding natural tissue. The choice of materials for the acetabular shell 110 and the screw hole plug 132 facilitates such deformation, as set forth above in connection with the embodiment of FIGS. 1 through 4. Here again, the seal provided by tapered portion 152 and tapered seat 154 may be characterized as a generally fluid-tight seal effective in minimizing the passage through the plugged screw hole 130 of debris of all particle sizes encountered during the service life of the prosthetic implant.

Once seated, the screw hole plug 132 does not protrude outwardly beyond the outer surface 112 or inwardly beyond the inner surface 114 of the acetabular shell 110. Sufficient clearance is provided at each end 144 and 146 of the screw hole plug 132 to enable appropriate seating of the acetabular shell 110 at the prepared implant site and appropriate seating of a bearing member within the interior of the acetabular shell 110.

Figure 7:
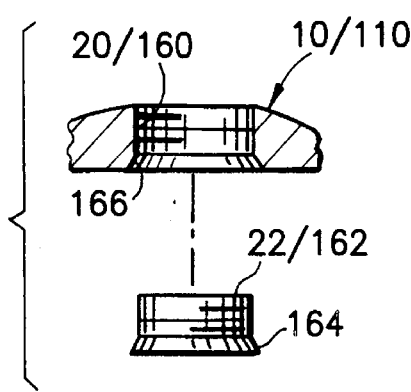
FIG. 7 is an exploded fragmentary view of a portion of either FIG. 2 or FIG. 5.

As in the earlier-described embodiment of FIGS. 1 through 4, a threaded opening 160 at the top of the domed configuration of acetabular shell 110 is closed by means of a dome plug 162. As best seen in FIG. 7, both dome plugs 22 and 162 are provided with a tapered sealing flange 164, which tapered sealing flange 164 engages a corresponding seat 166 in the acetabular shell 10 or 110 adjacent the dome opening 20 or 160 and is deformed upon seating of the dome plug 22 or 162 to complete a suitable seal, as described above in connection with the screw hole plug sealing means, between the dome plug 22 or 162 and the respective threaded opening 20 or 160. The dome plug 22 or 162 is seated so that some clearance is provided below the dome plug 22 or 162, as at 170, for enabling appropriate seating of the bearing member 16, and some clearance is provided above the dome plug 22 or 162, as at 172, for enabling proper seating of the acetabular shell 10 or 110 within the natural bone at the implant site.

It will be seen that the improvement of the present invention attains the objects and advantages summarized above; namely: Provides the surgeon with the ability to choose a particular acetabular shell securement interoperatively, in response to a direct evaluation of the conditions at the implant site, during the implant procedure, without the necessity of interchanging complete acetabular shells; reduces the time required for the implant of an acetabular shell, as well as the expense involved in the implant procedure; enables increased effectiveness in the securement of an acetabular shell in a hip prosthesis without undue prolongation of the implant procedure; reduces the cost of providing an appropriate acetabular shell configuration for a particular implant site; provides the surgeon with added convenience and increased options for securement of an acetabular shell, during the actual implant procedure, so as to better enable accommodation to the conditions encountered at a particular implant site; effectively minimizes the migration of debris ordinarily emanating from the bearing member of the acetabular cup component to the surrounding natural tissue, during the service life of the hip prosthesis; enables exemplary performance in an acetabular cup component over an extended service life.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. An improvement in an acetabular cup component of a prosthetic hip implant, the acetabular cup component having an acetabular shell which receives a bearing member within the acetabular shell, the acetabular shell having an inner surface defining an interior of the acetabular shell for receiving the bearing member, an outer surface for engagement with the natural bone at an implant site, and at least one bone screw hole in the acetabular shell, the bone screw hole extending through the acetabular shell from the inner surface to the outer surface of the acetabular shell, the improvement enabling the interoperative selection of implanting the acetabular shell without the employment of a bone screw or with the employment of at least one bone screw for assisting securement of the acetabular shell within the natural bone at the implant site, the improvement comprising:

a plug for seating in the bone screw hole to close the bone screw hole, the plug including fastener means for engaging the acetabular shell to fasten the plug within the bone screw hole, and sealing means for engaging the acetabular shell essentially to seal the bone screw hole against the migration of debris from the bearing member through the bone screw hole in the direction from the inner surface to the outer surface;

the plug having a length extending in a direction axially between the inner surface and the outer surface of the acetabular shell, when the plug is seated within the bone screw hole in the acetabular shell, the length being such that the plug does not protrude beyond the outer surface of the acetabular shell when the plug is seated within the bone screw hole;

the fastener means including a screw thread on the plug and operator means for being selectively operated from the interior of the acetabular shell to selectively release the screw thread of the plug from the bone screw hole for removal of the plug through the interior of the acetabular shell to thereby selectively open the bone screw hole for reception of the bone screw after engagement of the acetabular shell with the natural bone at an implant site.

2. The improvement of claim 1 wherein the fastener means includes a counterpart screw thread in the acetabular shell complementary to the screw thread on the plug.

3. The improvement of claim 2 wherein the counterpart screw thread is located in the bone screw hole.

4. The improvement of claim 3 wherein the bone screw hole includes a bore adjacent the outer surface of the acetabular shell and a countersink adjacent the inner surface of the acetabular shell, and the counterpart screw thread is located along the bore.

5. An improvement in an acetabular cup component of a prosthetic hip implant, the acetabular cup component having an acetabular shell which receives a bearing member within the acetabular shell, the acetabular shell being constructed of a biocompatible metal having a given hardness and including an inner surface defining an interior of the acetabular shell for receiving the bearing member, an outer surface for engagement with the natural bone at an implant site, and at least one bone screw hole in the acetabular shell, the bone screw hole extending through the acetabular shell from the inner surface to the outer surface of the acetabular shell and including a bore adjacent the outer surface of the acetabular shell and a countersink adjacent the inner surface of the acetabular shell, the improvement enabling the interoperative selection of implanting the acetabular shell without the employment of a bone screw or with the employment of at least one bone screw for assisting securement of the acetabular shell within the natural bone at the implant site, the improvement comprising:

a plug for seating in the bone screw hole to close the bone screw hole, the plug including fastener means for engaging the acetabular shell to fasten the plug within the bone screw hole, the fastener means including a screw thread on the plug and a counterpart screw thread complementary to the screw thread on the plug and located along the bore of the bone screw hole in the acetabular shell, and sealing means for engaging the acetabular shell essentially to seal the bone screw hole against the migration of debris from the bearing member through the bone screw hole in the direction from the inner surface to the outer surface;

the plug being constructed of a material having a hardness greater than the given hardness of the material of the acetabular shell such that upon seating of the plug in the bone screw hole, the screw thread on the plug deforms a corresponding portion of the acetabular shell to establish the counterpart screw thread;

the fastener means further including operator means for being selectively operated from the interior of the acetabular shell to selectively release the plug from the bone screw hole for removal of the plug through the interior of the acetabular shell to thereby selectively open the bone screw hole for reception of the bone screw.

6. The improvement of claim 5 wherein the screw thread on the plug is a microthread.

7. The improvement of claim 3 wherein the bone screw hole includes a bore adjacent the outer surface of the acetabular shell and a countersink adjacent the inner surface of the acetabular shell, and the counterpart screw thread is located along the countersink.

8. The improvement of claim 1 wherein the sealing means includes a tapered portion on the plug for engaging a corresponding sealing portion of the acetabular shell in sealing engagement when the plug is seated in the bone screw hole.

9. The improvement of claim 8 wherein the tapered portion is tapered from a smaller diameter adjacent the outer surface of the acetabular shell toward a larger diameter adjacent the inner surface of the acetabular shell, when the plug is seated within the bone screw hole.

10. An improvement in an acetabular cup component of a prosthetic hip implant, the acetabular cup component having an acetabular shell which receives a bearing member within the acetabular shell, the acetabular shell having an inner surface defining an interior of the acetabular shell for receiving the bearing member, an outer surface for engagement with the natural bone at an implant site, and at least one bone screw hole in the acetabular shell, the bone screw hole extending through the acetabular shell from the inner surface to the outer surface of the acetabular shell and including a bore adjacent the outer surface of the acetabular shell and a countersink adjacent the inner surface of the acetabular shell, the improvement enabling the interoperative selection of implanting the acetabular shell without the employment of a bone screw or with the employment of at least one bone screw for assisting securement of the acetabular shell within the natural bone at the implant site, the improvement comprising:

a plug for seating in the bone screw hole to close the bone screw hole, the plug including fastener means for engaging the acetabular shell to fasten the plug within the bone screw hole, and sealing means for engaging the acetabular shell essentially to seal the bone screw hole against the migration of debris from the bearing member through the bone screw hole in the direction from the inner surface to the outer surface, the sealing means including a tapered portion on the plug for engaging a corresponding sealing portion of the acetabular shell in sealing engagement when the plug is seated in the bone screw hole, the tapered portion being tapered from a smaller diameter adjacent the outer surface of the acetabular shell toward a larger diameter adjacent the inner surface of the acetabular shell, when the plug is seated within the bone screw hole, the corresponding sealing portion of the acetabular shell being located along the bore of the bone screw hole;

the fastener means including a screw thread on the plug and operator means for being selectively operated from the interior of the acetabular shell to selectively release the screw thread of the plug from the bone screw hole for removal of the plug through the interior of the acetabular shell to thereby selectively open the bone screw hole for reception of the bone screw.

11. The improvement of claim 9 wherein the bone screw hole includes a bore adjacent the outer surface of the acetabular shell and a countersink adjacent the inner surface of the acetabular shell, and the corresponding sealing portion of the acetabular shell is located between the bore and the countersink.

12. The improvement of claim 9 wherein the acetabular shell is constructed of a biocompatible metal having a given hardness, and the plug is constructed of a material having a hardness greater than the given hardness of the material of the acetabular shell such that upon seating of the plug in the bone screw hole, the tapered portion on the plug deforms the material of the acetabular shell to establish the corresponding sealing portion of the acetabular shell and seal the bone screw hole.

13. The improvement of claim 1 wherein the length of the plug is less than the axial distance between the inner surface and the outer surface of the acetabular shell so that the plug does not protrude beyond either one of the inner surface and the outer surface of the acetabular shell when the plug is seated within the bone screw hole.

14. The improvement of claim 1 including a plurality of bone screw holes and a corresponding plurality of screw hole plugs.

15. The improvement of claim 14 wherein the plurality of bone screw holes are arrayed throughout the acetabular shell.

* * * * *

UNITED STATES PATENT AND TRADEMARK OFFICE
CERTIFICATE OF CORRECTION

PATENT NO. : 5,571,198
DATED : November 5, 1996
INVENTOR(S) : David A. Drucker, Robert G. Collins, and Nicholas N.G. Dong It is certified that error appears in the above-indentified patent and that said Letters Patent is hereby corrected as shown below:

In the Title [54], and col. 1, line 2, change "HOLDS" to --HOLES--.

Column 3, line 15, change "FIGS," to --FIGS.--.

Column 4, line 45, change "use!" to --use--.

Signed and Sealed this

Eleventh Day of February, 1997

Attest:

BRUCE LEHMAN

Attesting Officer     Commissioner of Patents and Trademarks